United States Patent [19]

Martin

[11] Patent Number: 4,552,531
[45] Date of Patent: Nov. 12, 1985

[54] GAUGED ROOT CANAL CONDENSER SPREADER

[76] Inventor: Howard Martin, 909 Pershing Dr., Silver Spring, Md. 20910

[21] Appl. No.: 671,908

[22] Filed: Nov. 16, 1984

[51] Int. Cl.$^4$ ............................................. A61C 3/00
[52] U.S. Cl. .................................. 433/147; 433/141; 40/913
[58] Field of Search .................. 433/147, 141, 72, 75, 433/102, 224; 40/913

[56] References Cited

U.S. PATENT DOCUMENTS

| | | | |
|---|---|---|---|
| 797,270 | 8/1905 | Dreher | 433/141 |
| 1,067,015 | 7/1913 | Fowler | 433/102 |
| 1,356,372 | 10/1920 | Kelly | 433/147 |
| 1,984,839 | 12/1934 | Murray | 40/913 |
| 3,430,345 | 3/1969 | Abreu | 433/147 |
| 3,935,640 | 2/1976 | Cohan | 433/75 |
| 4,060,897 | 12/1977 | Greenstein | 433/141 |

Primary Examiner—John J. Wilson
Attorney, Agent, or Firm—Walter G. Finch

[57] ABSTRACT

The invention is an improved dental instrument for root canal dental treatment. The improved instrument is a combined root canal condenser and spreader instrument which makes it possible for the dentist to do the treatment work with one instrument instead of constantly changing back and forth between two instruments. In addition, the combined instrument uses a common handle with removable and replaceable working ends of the instrument when different sizes of instruments are required for the tooth being treated or for the stage at which the tooth is being treated. The removable and replaceable working ends of the instrument are gauged marked so that the dentist can gauge the depth at which the dental work must be done and at which the following stages of the work are being done in order to assure a fully spread and condensed dental material in the tooth. The gauged root canal condenser spreader consists of a handle member, a removable and replaceable condenser instrument end or tip, a removable and replaceable spreader instrument end, and easily visable gauge markings on each of the removable and replaceable condenser and spreader instrument ends, respectively.

7 Claims, 4 Drawing Figures

GAUGED ROOT CANAL CONDENSER SPREADER

BACKGROUND AND SUMMARY OF THE INVENTION

The invention is an improved dental instrument for root canal dental treatment, and in particular a combined instrument of both a condenser instrument and a spreader instrument. Specifically, it is a combined dental instrument with a common handle with removable and replaceable instrument ends or tips which are gauged marked to indicate the depth at which the dental work is being performed as well as size indication.

In performing root canal work there is a phase at which the prepared root canal must be filled with a recognized dental filling material. In the prior art two instruments have been used for this work, a condenser and a spreader. In using the two instruments it has meant that the dentist must alternately put down one instrument and then pick up the other instrument to do the work. This method has two distinct disadvantages, one is the loss of time in an expensive procedure and the other is that the filling material has a tendency to stiffen or harden during the delay between the manual change of instruments.

In the present invention both instruments, the condenser and the spreader, are each on opposite ends of a common handle. The change from one instrument to the other is performed quickly by a flip of the instrument in the hand, a fast movement of the fingers with some minor movement of the wrist. The change is so rapid that the filling material is essentially worked almost constantly so that it does not stiffen or harden to any perceptible degree.

In addition, dental instruments used in the preparation of the root canal prior to the filling procedure are in a plurality of diametrical sizes as the tooth is prepared at different depths. In a like manner, the condensers and spreaders are similarly diametrically sized for the various diametrical dimensions of the prepared root canal at the different depths.

In the prior art each condenser and each spreader of each size had its own handle, a very expensive arrangement. In the present arrangement a common handle member is used with recesses or pockets in each end into which removable and replaceable condensers and spreaders can be inserted to snap into place. Thus, the expense of a plurality of handles is eliminated.

The plurality of sizes of the condensers and the spreaders is reproduced in pairs in the present invention, a pair being a spreader and a condenser of the same size as a removable and replaceable snap-in set, one spreader and one condenser of like size.

Breakage and bending of the delicately sized condensers and spreaders occurs and with the snap-in type of instrument ends the economical savings of the present invention is readily apparent when the handle of such instruments is not lost with the breakage of the condenser or spreader end. The versatile handle has economic as well as performance advantages.

The condensers and spreaders of the present invention are color coded to match the root canal preparation instruments so that the dentist can readily select the size of condenser and spreader tip in accordance with the size of the preparation instrument used to prepare the root canal for filling. This assures the proper condensing and spreading of the filling material for the most efficient and proper filling of the root canal. This matching of condensers and spreaders by the color code also assures that the proper standardized tapes diameter is used for the work to be done by the condenser and spreader.

In the prior art some attempt has been made at line or groove or score working of dental instruments for depth, but the lines or grooves or scores are difficult to see or read and easily mistaken. Also, the line or groove or score marking increases the chances of breakage because of the cut in the surface of the very thin and fine diameters of the instruments. This would be especially true in the case of condensers and spreaders because of the pressure exerted on the instruments to do the dental work involved, plus the flexing and bending which occurs.

The operating heads may be either uniangular or bayonet style. The condensers are smooth, flat ended, and slightly tapered and used to condense the filling material, such as gutta percha, vertically in a root canal. The spreaders are also smooth and pointed, and tapered for laterally condensing the filling material in a root canal by a vertical rotary motion.

In the present invention part of the color coding is to match up the improved condenser spreader with the size of the root canal files used to prepare the root canal prior to filling. Thus, by this color code matching the diameter and angle of the improved condenser spreader will match the diameter and angle of the root canal preparation instrument and assure a completely filled root canal cavity. This method standardizes the procedure.

In the prior art condenser and spreader instruments were of two types, those known as finger instruments and those known as long handled instruments. The finger type instruments could not exert enough pressure to adequately condense and spread the filling material and the long handled instruments exerted too much pressure and often cracked the root structure of the tooth. With the present inventions matched sizes of instruments as to diameter and angle, the filling procedure is more efficient with a reduction in encountered problems.

The color coding of the condensers and spreaders of the present invention provides the dentist with immediate information as to which size to use in order to match the root canal preparation instrument without a trial and error method. International Standard color codes are used as described later hereinafter.

In a like manner the color code of the size of the instrument is also used in the present invention to color code the depth. This provides the dentist with information in order to match up the depth of the root canal preparation with the depth of the filling to be made by the condenser and spreader. Thus, the dentist knows immediately how close to the tip of the root of the tooth he prepared and also how close he was for the correct filling of the root canal.

It is this depth of penetration that enables the filling material to be properly condensed and spread for an effective filling. Scientific studies show that the proper depth of the condenser and spreader is the key to a successful root canal filling.

It is, therefore, an object of this invention to provide a dental instrument that combines both a condenser instrument and a spreader instrument for root canal treatment.

It is another object of this invention to provide a dental instrument that has a common handle for both a condenser instrument and a spreader instrument.

It is also an object of this invention to provide a dental instrument that has removable and replaceable condenser and spreader tips.

It is a further object of this invention to provide a dental instrument in a plurality of sizes for both the condenser and the spreader tips.

It is still another object of this invention to provide a dental instrument that is color coded to relate the size of the condenser and spreader tips to the size of the root canal preparation instruments.

It is yet another object of this invention to provide a dental instrument that is gauge marked to indicate depth at which dental work is being performed.

It is yet still another object of this invention to provide a dental instrument that color codes the gauge markings for easy and visable reading and relation to the size of the instrument.

Further objects and advantages of the invention will become more apparent in light of the following description of the preferred embodiments.

DESCRIPTION OF THE PREFERRED EMBODIMENTS

Figure 1:
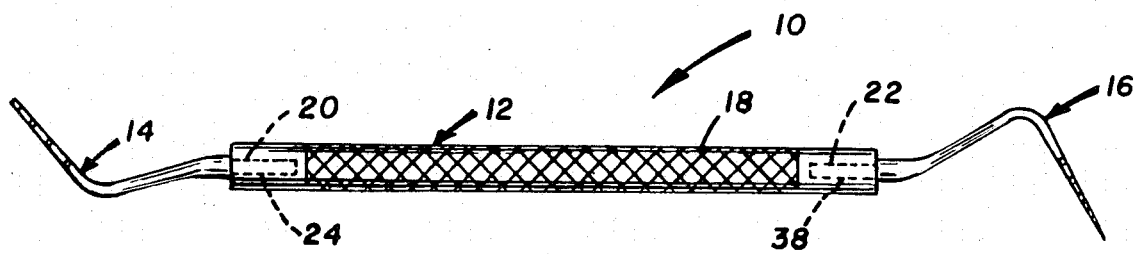
FIG. 1 is a side view of a combined condenser spreader dental instrument.

Referring now to the drawings and particularly to FIG. 1, a gauged root canal condenser spreader is shown at 10.

The gauged root canal condenser spreader 10 dental instrument, hereinafter referred to as the gauged condenser spreader 10, consists of a handle component 12, a condenser tip component 14, and a spreader tip component 16. The details of the elements of these components is described hereinafter.

The condenser tip component 14 and the spreader tip component 16 are snap fits into respective ends of the handle component 12 as shown in FIG. 1. The snap fit may be made secure in the handle component 12 by a set screw means (not shown) or a detent means (not shown) or by other suitable securing means if desired to retain the condenser tip component 14 and the spreader tip component 16 in a tighter manner.

The handle component 12 consists of the elongated rod-like body with suitable knurling 18 on the exterior surface and with suitable sockets 20 and 22, one in each end, as described hereinafter.

The socket 20 in one end of the handle component 12 is suitably configured to fit and mate with the coupling shank 24 of the condenser tip component 14. The socket 22 in the opposite end of the handle component 12 is suitably configured to fit and mate with the coupling shank 38 of the condenser tip component 16.

It is to be noted and understood that the cross sectional configurations of the coupling shanks 24 and 38, respectively, and their mating sockets 20 and 22, respectively, may be square, triangular, or any other suitable geometric configuration, and that such variations are within the scope and intent of the present invention.

Figure 2:
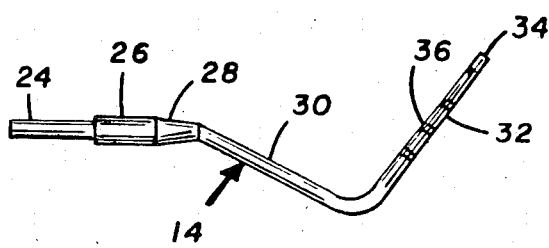
FIG. 2 is an enlarged view of a first embodiment of a condenser tip for the combined condenser spreader dental instrument of FIG. 1.

Turning now to FIG. 2 the condenser tip component 14 consists of the aforementioned coupling shank 24, a short body section 26 adjoining the coupling shank 24, a tapered section 28 making the transition from the body section 26 to the instrument bend portion 30, and the instrument operating condenser tip 32 which is suitably affixed at an adjoining bend to the instrument bend portion 30.

The aforementioned elements of the condenser tip component 14 are essentially integrally and monolithically one piece, however, it is to be understood that it is within the scope and intent of this invention for these elements to be separate pieces suitably affixed to each other in the sequence shown and described.

The bend between the tapered section 28 and the bend portion 30 is substantially an angle of 45° plus or minus 15°, however, it is to be understood that variations from such an angle and tolerance are within the scope and intent of this invention.

The bend from the bend portion 30 to the instrument operating condenser tip 32 is substantially 90°, however, it is also within the scope and intent of the invention to have variations from the angle of 75°±15°.

The tip end 34 of the instrument operating condenser tip 32 is blunt or flat, but it is to be understood that the configuration of the tip end 34 may also be rounded 52.

Gauge markings 36 are color coded and are described in detail hereinafter. The gauge markings 36 indicate by color the size, as hereinafter described, and by location indicate the depth of the root canal cavity at the point where dental work is being performed, as hereinafter described.

Figure 3:
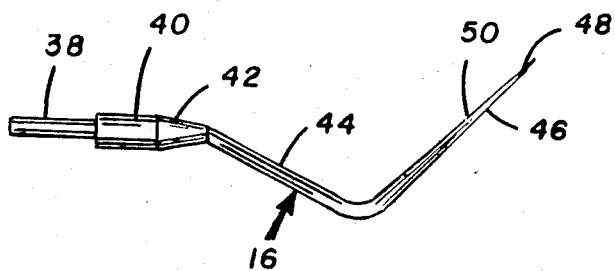
FIG. 3 is an enlarged view of a spreader tip for the combined condenser spreader dental instrument of FIG. 1.
Figure 4:
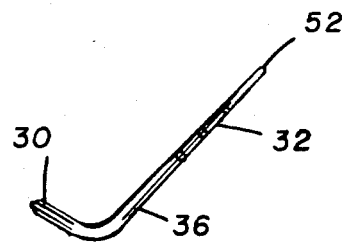
FIG. 4 is a partial enlarged view of a second embodiment of a condenser tip of FIG. 1.

Turning now to FIG. 3 the spreader tip component 16 consists of the aforementioned coupling shank 38, a short body section 40 adjoining the coupling shank 38, a tapered section 42 making the transition from the body section 40 to the instrument bend portion 44, and the instrument operating spreader tip 46 which is suitably affixed at an adjoining bend to the instrument bend portion 44.

The aforementioned elements of the spreader tip component 16 are essentially integrally and monolithically one piece, however, it is to be understood that it is within the scope and intent of this invention for these elements to be separate pieces suitably affixed to each other in the sequence shown and described.

The bend between the tapered section 42 and the bend portion 44 is substantially an angle of 45° plus or minus 15°, however, it is to be understood that variations from such an angle and tolerances are within the scope and intent of this invention.

The bend from the bend portion 44 to the instrument operating spreader tip 46 is substantially 90°, however, it is also within the scope and intent of the invention to have variations from the angle of 75°±15°.

The tip end 48 of the instrument operating spreader tip 46 is pointed.

Gauge markings 50 are color coded and are described in detail hereinafter. The gauge markings 50 indicate by color the size, as hereinafter described, and by location indicate the depth of the root canal cavity at the point where dental work is being performed, as hereinafter described.

Turning now to a discussion of the color coding meanings as part of the instrument operating condenser tip 32 and the instrument operating spreader tip 46, as noted hereinbefore the color codings serve several purposes.

First of all, the color codings on both the instrument operating condenser tip 32 and on the instrument operating spreader tip 46 are matched in color so that the two instruments (condenser tip 32 and spreader tip 46) may be used in matched pairs.

The color coding marks or bands on the condenser tip 32 and on the spreader tip 46 indicate the depth of the point of work being performed in the root canal cavity, the depth marking are described hereinafter. Note that the colored bands do not cut into the condenser tip 32 or the spreader tip 46 and weaken the structure as was described hereinbefore for line or groove markings.

The colors of the coding for the condenser tip 32 and the spreader tip 46 match the color coding on dental instruments used for preparing the root canals prior to filling. Thus, the file type instruments color coding indicates both size, such as the diameter, at the end of the working area in the root canal as well as a depth. When the condenser tip 32 and the spreader tip 46 of the present invention is selected for filling at that depth point, selection by a matching color code with the root canal preparation instruments assures a proper sizing and depth to adequately and properly fill the prepared root canal.

As to the depth gauge markings the condenser tip 32 and the spreader tip 46 have the first gauge marking set at 17 mm from the working end of the two tips 32 and 46, respectively. Thereafter, the gauge markings are set at 19 mm, 21 mm, and 23 mm. The overall length of the condenser tip 32 and the spread tip 46 is normally at least 25 mm or more. However, it is to be understood that it is within the scope and intent of the present invention to vary the condenser tip 32 and the spreader tip 46 lengths to other than 25 mm and to likewise use more than or less than the number of gauge markings shown hereinabove, or at some other dimension from the ends of the respective tips 32 and 46. The cited dimensional locations are for purposes of establishing or using a standard.

As to the colors regarding the size, particularly in regard to the tip end 34 of the condenser tip 32, the use of international specification colors is used. In this regard the color refers to the size of the tip end, and the same color is used for the gauge markings 36 and 50, respectively, in order to use the condenser tip component 14 in a matched set with the corresponding spreader tip component 16. The color codes are provided hereinafter.

Each color of the color code indicates a tip size or dimension. For example: white indicates a tip size of 15, which in tenths of a mm, in other words size 15 is 0.15 mm in diameter; yellow indicates a tip size of 20, or 0.20 mm in diameter. The color also indicates the overall depth of the root canal preparation.

As the condenser tip 32 and the spreader tip 46 taper from the juncture with bend portions 30 and 44, respectively, to the working ends 34 and 48, respectively, the taper is constant for each size. For condenser tips 32 and spreader tips 46 of this invention, the total taper from the working ends 34 and 36, respectively, to extreme other end where the condenser tip 32 and the spreader tip 46 join the respective bend portions 30 and 44, the total change in diamter due to the taper is 0.32 mm.

In the listing below of color codes, the details are as described hereinbefore. The listing provides the colors of the code, the tip size 34 as a numeral for the condenser tip 32, the diameter dimension of the tip size in mm at the tip end 34, and the diameter dimension of the condenser tip 32 where it joins the bend portion 30.

| COLOR CODING | | | |
|---|---|---|---|
| Color | Size Numeral | Tip End Dimension | Tip Top Dimension |
| White | 15 | 0.15 mm | 0.47 mm |
| Yellow | 20 | 0.20 mm | 0.52 mm |
| Red | 25 | 0.25 mm | 0.57 mm |
| Blue | 30 | 0.30 mm | 0.62 mm |
| Green | 35 | 0.35 mm | 0.67 mm |
| Black | 40 | 0.40 mm | 0.72 mm |
| White | 45 | 0.45 mm | 0.77 mm |
| Yellow | 50 | 0.50 mm | 0.82 mm |
| Blue | 60 | 0.60 mm | 0.92 mm |
| Green | 70 | 0.70 mm | 1.02 mm |
| Black | 80 | 0.80 mm | 1.12 mm |
| Green | 90 | 0.90 mm | 1.22 mm |
| White | 100 | 1.00 mm | 1.32 mm |

Thus, the condenser tip 32 and the spreader tip 46 are color coded for matching pairs, the taper and diameter of the condenser tip 32 match the root canal hand preparation instrument taper and diameter by the color code, and the color code also provides for easy reading of the depth at which the dental work is being performed. The repetition of the color codes in the large sizes can be further separated by the size numeral marked thereon.

The gauged condenser spreader may be made from stainless steel or chrome plated brass or any other suitable material.

As can be readily understood from the foregoing description of the invention, the present structure can be configured in different modes to provide the ability to perform gauged root canal condenser and spreader operations.

Accordingly, modifications and variations to which the invention is susceptible may be practiced without departing from the scope and intent of the appended claims.

What is claimed is:

1. A dental instrument for root canal work, comprising:
    a handle, said handle having geometrically configured socket-like cavities in each end thereof, said handle being elongated and rod-like in configuration and having suitable knurling on the outside surface thereof;
    a first dental instrument component, said first dental instrument component having a capability for performing dental condensing operations in prepared root canals of teeth, said first dental instrument component having a first end and a second end, said first end of said first dental instrument component being geometrically configured into a shaft-like coupling end, said geometrically configured shaft-like coupling end being so sized and configured so as to be removably inserted into one of said geometrically configured socket-like cavities in said handle by a snap fit, said second end of said first dental instrument component being configured into a tapered condenser portion to perform said condensing operations in said prepared root canals, said first dental instrument component between said geometrically configured shaft-like coupling end and said tapered condenser portion thereof has a short body member portion, a tapered transition portion, and a bend portion, in that sequence, said geometrically configured shaft-like coupling end, said short body portion, said tapered transition portion, said bend portion, and said tapered condenser portion all being integral and monolithic in that sequence;

a second dental instrument component, said second dental instrument component having a capability for performing dental spreader operations in prepared root canals of teeth, said second dental instrument component having a first end and a second end, said first end of said second dental instrument component being geometrically configured into a shaft-like coupling end, said geometrically configured shaft-like coupling end being so sized and configured so as to be removably inserted into the other of said geometrically configured socket-like cavities in said handle by a snap-fit, said second end of said second dental instrument component being configured into a tapered portion to perform said spreader operations in said root canals, said second dental instrument component between said geometrically configured shaft-like coupling end and said tapered spreader portion thereof has a short body member portion, a tapered transition portion, and a bend portion, in that sequence, said geometrically configured shaft-like coupling end, said short body portion, said tapered transition portion, said bend portion, and said tapered spreader portion all being integral and monolithic in that sequence; and a plurality of color code markings, said plurality of color code markings being applied to said second end of said first and second dental instrument components, respectively, to indicate matching pairs and size and depth measurements in said prepared root canals.

2. A dental instrument as recited in claim 1, wherein the distal end of said second end of said first dental intrument component is flat and blunt-like in configuration.

3. A dental instrument as recited in claim 1, wherein the distal end of said second end of said first dental instrument component is rounded in configuration.

4. A dental instrument as recited in claim 1, wherein the distal end of said second end of said second dental instrument component is pointed.

5. A dental instrument as recited in claim 1, wherein each code marking of said plurality of code markings are each band-like and encircle said tapered portion of said second ends of said first and second dental instrument components, respectively.

6. A dental instrument as recited in claim 1, wherein said plurality of code markings are applied to said second end of said first and second dental instruments, respectfully, to indicate sizes in accordance with the following table:

| COLOR CODING | | | |
|---|---|---|---|
| Color | Size Numeral | Tip End Dimension | Tip Top Dimension |
| White | 15 | 0.15 mm | 0.47 mm |
| Yellow | 20 | 0.20 mm | 0.52 mm |
| Red | 25 | 0.25 mm | 0.57 mm |
| Blue | 30 | 0.30 mm | 0.62 mm |
| Green | 35 | 0.35 mm | 0.67 mm |
| Black | 40 | 0.40 mm | 0.72 mm |
| White | 45 | 0.45 mm | 0.77 mm |
| Yellow | 50 | 0.50 mm | 0.82 mm |
| Blue | 60 | 0.60 mm | 0.92 mm |
| Green | 70 | 0.70 mm | 1.02 mm |
| Black | 80 | 0.80 mm | 1.12 mm |
| Green | 90 | 0.90 mm | 1.22 mm |
| White | 100 | 1.00 mm | 1.32 mm |

7. A dental instrument as recited in claim 6 and additionally, a code numeral, said code numeral being the same as said size numeral for each said color code, said code numeral being placed upon said handle component to differentiate the sizes where said color code color is repeated in the large sizes.

* * * * *